United States Patent [19]

Coughlin

[11] Patent Number: 4,579,830

[45] Date of Patent: Apr. 1, 1986

[54] ENHANCED CATALYST FOR CONVERTING SYNTHESIS GAS TO LIQUID MOTOR FUELS

[75] Inventor: Peter K. Coughlin, Yorktown Heights, N.Y.

[73] Assignee: Union Carbide Corporation, Danbury, Conn.

[21] Appl. No.: 625,372

[22] Filed: Jun. 27, 1984

[51] Int. Cl.$^4$ .......................... B01J 29/08; B01J 27/18
[52] U.S. Cl. ........................................ 502/66; 502/74; 502/213
[58] Field of Search ............................ 502/66, 74, 213; 518/714

[56] References Cited

U.S. PATENT DOCUMENTS

| | | | |
|---|---|---|---|
| 3,013,990 | 12/1961 | Breck et al. | 252/455 |
| 4,086,262 | 4/1978 | Chang et al. | 260/449.6 R |
| 4,138,326 | 2/1979 | Swift et al. | 502/66 X |
| 4,157,338 | 6/1979 | Haag et al. | 260/449 R |
| 4,172,843 | 10/1979 | Dwyer et al. | 260/449.6 R |
| 4,180,516 | 12/1979 | Chang et al. | 260/449 R |
| 4,199,522 | 4/1980 | Murchison et al. | 518/715 X |
| 4,207,248 | 6/1980 | Butter et al. | 260/449.6 R |
| 4,279,830 | 7/1981 | Haag et al. | 518/700 |
| 4,293,446 | 10/1981 | Butter et al. | 502/66 |
| 4,340,503 | 7/1982 | Rao et al. | 252/459 |
| 4,440,871 | 4/1984 | Lok et al. | 502/214 |

FOREIGN PATENT DOCUMENTS 874373 2/1979 Belgium .
2077754 6/1981 United Kingdom .

OTHER PUBLICATIONS

"The Fischer-Tropsch Synthesis in the Liquid Phase''-Catal. Rev.-Sci. Eng., 21(2), 225-274, (1980), Herbert Kolbel and Milos Ralek, pp. 225, 243-247.

Primary Examiner—Carl F. Dees
Attorney, Agent, or Firm—Alvin H. Fritschler

[57] ABSTRACT

The conversion of synthesis gas to liquid molar fuels by means of a cobalt Fischer-Tropsch catalyst composition is enhanced by the addition of molybdenum, tungsten or a combination thereof as an additional component of said composition. The presence of the additive component increases the olefinic content of the hydrocarbon products produced. The catalyst composition can advantageously include a support component, such as a molecular sieve, co-catalyst/support component or a combination of such support components.

27 Claims, No Drawings

ENHANCED CATALYST FOR CONVERTING SYNTHESIS GAS TO LIQUID MOTOR FUELS

STATEMENT

The Government of the United States of America has rights to this invention pursuant to Contract No. DE-AC22-81PC40077 awarded by the U.S. Department of Energy.

BACKGROUND OF THE INVENTION

1. Field of the Invention

The invention relates to the conversion of synthesis gas to hydrocarbons. More particularly, it relates to the conversion in such synthesis gas to $C_5+$ hydrocarbons suitable for use as liquid motor fuels.

2. Description of the Prior Art

It is well known in the art that synthesis gas, i.e., hydrogen and carbon monoxide, can be converted to hydrocarbons in the presence of a variety of transition metal catalysts. Thus, certain Group VIII metals, particularly iron, cobalt, ruthenium and nickel, are known to catalyze the conversion of CO and hydrogen, also referred to as syngas, to hydrocarbons. Such metals are commonly called Fischer-Tropsch catalysts. While the use of nickel preferentially produces methane upon conversion of syngas, the use of iron, cobalt and ruthenium tends to produce hydrocarbon mixtures consisting of hydrocarbons having a larger carbon number than methane, as determined by a number of analytical means including mass spectrographic analysis of individual components and the boiling point curve method. At higher reaction temperatures, all Fischer-Tropsch catalysts tend to produce gaseous hydrocarbons, and it is readily feasible to select processing conditions to produce methane as the principal product. At lower temperatures, and usually at higher pressures, however, iron, cobalt and ruthenium produce hydrocarbon mixtures consisting of larger hydrocarbons. These products usually contain very long straight-chain hydrocarbon molecules that tend to precipitate as wax. Such wax material, boiling well beyond the boiling range of motor fuels, typically constitutes a significant fraction of the product produced in such catalytic conversion operations. Fischer-Tropsch catalysts have not been advantageously employed in the production of liquid hydrocarbon motor fuels, therefore, instead commonly producing either principally gaseous hydrocarbons, on the one hand, or hydrocarbons containing an unacceptably large amount of wax on the other. In addition, the gasoline boiling hydrocarbon fraction that has been produced has an unacceptably low octane number.

In light of such circumstances, efforts have been made to improve the performance of Fischer-Tropsch catalysts for use in various desired syngas conversions. For example, the Breck et al. patent, U.S. Pat. No. 3,013,990, discloses the use of zeolitic molecular sieves containing a Fischer-Tropsch catalyst as improved catalyst compositions. Thus, Type A, X and Y molecular sieves loaded with iron or cobalt are shown to be suitable Fischer-Tropsch hydrocarbon synthesis catalysts, as for the production of methanol from syngas. Also with respect to the conversion of syngas, Fraenkel et al., U.S. Pat. No. 4,294,725, teach that zeolites A and Y loaded with cobalt, incorporated by ion exchange and reduced in-situ with cadmium, serve as useful catalysts of the Fischer-Tropsch type. Those skilled in the art will appreciate that such catalyst materials tend to be relatively expensive and, in any event, do not produce hydrocarbon products advantageous for use as liquid motor fuels.

Efforts have also been made to improve Fischer-Tropsch catalyst performance by preparing intimate mixtures of Fischer-Tropsch metals, such as iron, with an acidic crystalline aluminosilicate, such as ZSM-5. The Chang et al. patents, U.S. Pat. No. 4,086,262, and U.S. Pat. No. 4,096,163, disclose such catalyst compositions employed in the conversion of synthesis gas to hydrocarbon mixture useful in the manufacture of heating fuels, gasoline, aromatic hydrocarbons and chemical intermediates. When it is desired to convert syngas specifically to hydrocarbons boiling in the jet fuel+diesel oil boiling range, however, such an approach is not suitable, experiencing an effective limitation at $C_{10}$ carbon number as was the case using ZSM-5 in methanol conversion, as disclosed in the Owen et al. patent, U.S. Pat. No. 3,969,426.

While iron is the currently preferred Fischer-Tropsch catalyst component for use in syngas conversion operations, cobalt had originally been preferred because of its various desirable properties. Thus, cobalt has a higher level of catalytic activity in syngas conversion operations as well as a better selectivity to total motor fuels than is obtained using iron. Cobalt has certain product quality disadvantages, however, that have tended to discourage its use for syngas conversion operations. Thus, the hydrocarbon products obtained using cobalt catalysts are generally more paraffinic and waxy than the corresponding products obtained using iron as the Fischer-Tropsch catalyst. Such waxy products are much more difficult to upgrade, as by the use of a shape selective component in the Fischer-Tropsch catalyst composition in accordance with known practice, than would be a more olefinic hydrocarbon conversion product of syngas conversion operations.

It is desirable, therefore, that improvements be made in the art to enable cobalt to be more advantageously employed as a Fischer-Tropsch catalyst for syngas conversion operations. The prior art developments relating to the use of cobalt catalysts for applications other than Fischer-Tropsch catalysts do not appear relevant to the problems associated with the Fischer-Tropsch conversion of syngas to liquid motor fuels. Thus, cobalt-molybdenum catalysts supported on alumina are the commonly employed commercial hydrotreating hydrode-sulfurization) catalysts. Such catalysts, generally containing 3–5% CoO and 15% $MoO_3$ on $Al_2O_3$, are not particularly relevant to Fischer-Tropsch catalysts. In another area of prior art activity, molybdenum and tungsten have been employed in Fischer-Tropsch synthesis reactions.

At a 1982 Material Research Society meeting, A. Brenner reported the use of molybdenum and tungsten as Fischer-Tropsch metals. Thus, molybdenum salts were reduced at a high temperature (1000° C.), and the reduced molybdenum was found to act as a very low activity Fischer-Tropsch metal. A somewhat more active catalyst can be formed by reducing molybdenum or tungsten carbonyl. Molybdic acid has also been tested as a promoter for iron Fisher-Tropsch catalysts as reported in the Fischer-Tropsch and Related Synthesis by H. Storch, N. Golumbic and R. Anderson, John Wiley & Sons, N.Y. 1951, however, the molybdic acid did not improve the activity of the iron catalyst. Storch et al also reported the testing of tungsten oxide promoters for iron Fischer-Tropsch catalysts, said promoters resulting in a shift of the product distribution toward high wax yields.

It is generally known in the art that manganese is effective in increasing the olefin content of hydrocarbon products obtained upon syngas conversion using an iron Fischer-Tropsch catalyst. Manganese is not effective, however, in producing more olefins when a cobalt Fischer-Tropsch catalyst is employed. Despite the various activities carried out in the art as indicated above, there remains a desire in the art for improvements rendering cobalt a more satisfactory Fischer-Tropsch catalyst for syngas conversion than it is at the present time. What is thus desired in the art is the development of an additive and/or an operating technique that will have a similar effect with respect to cobalt as has manganese with respect to iron catalysts.

It is an object of the invention, therefore, to provide an improved Fischer-Tropsch catalyst composition for use in the conversion of syngas to liquid motor fuels.

It is another object of the invention to provide an improved cobalt-based Fischer-Tropsch catalyst composition for said syngas conversion.

It is a further object of the invention to provide a cobalt Fischer-Tropsch syngas conversion catalyst and process capable of enhancing the olefinic content of the liquid hydrocarbon conversion products obtained.

With these and other objects in mind, the invention is hereinafter described in detail, the novel features thereof being particularly pointed out in the appended claims.

SUMMARY OF THE INVENTION

The olefinic content of the hydrocarbon products obtained during syngas conversion operations using cobalt as a Fischer-Tropsch catalyst is increased by the addition of a particular additive component to a cobalt catalyst composition. The catalyst composition is advantageously supported by a molecular sieve co-catalyst/support component capable of enhancing the desired conversion of syngas to liquid hydrocarbons useful or capable of conversion to desired motor fuels.

DETAILED DESCRIPTION OF THE INVENTION

The objects of the invention are accomplished by the admixing of a particular additive component with a cobalt-containing Fischer-Tropsch catalyst. Such additive is taken from the group consisting of molybdenum, tungsten and combinations thereof. As a result of the use of such an additive, the use of cobalt as a syngas conversion catalyst is enhanced as the resulting hydrocarbon products obtained are found to have a desirably higher olefinic content than is obtained in the absence of the use of the additive component. The suitability of the product liquid hydrocarbons obtained for use as motor fuels is thereby enhanced by the practice of the invention in conjunction with the use of cobalt with or without thorium promotion as a Fischer-Tropsch catalyst for syngas conversion. The synthesis gas, or syngas, treated in accordance with the practice of the invention generally comprises a mixture of hydrogen and carbon monoxide, usually together with smaller amounts of carbon dioxide, methane, nitrogen or other components as is well known in the art. Syngas is commonly produced by steam reforming of hydrocarbons or by the partial oxidation of coal and petroleum deposits, or by similar gasification of other carbonaceous fuels such as peat, wood and cellulosic waste materials. The hydrogen/carbon oxide volume ratio of such syngas is desirably in the range of from about 0.2/1 to about 6.0/1 prior to conversion to liquid motor fuels as herein disclosed and claimed. This ratio can be adjusted, if desired, by reaction of carbon monoxide with steam in the well-known water-gas shift reaction. If required, sulfur impurities can be removed from the syngas mixture by conventional means known in the art. It should also be noted that the syngas as described herein includes art-recognized equivalents, such as mixtures of carbon monoxide and steam, or of carbon dioxide and hydrogen, that can provide synthesis gas mixture by in-situu reaction under the operating conditions employed.

The invention as herein described is related to the use of cobalt admixed with the additive component referred to above, preferably thorium-promoted and preferably with a support component, particularly one that tends to further enhance the desired syngas conversion to liquid motor fuels as further described below. The additive component can be employed in an amount within the range of from about 1% to about 50 mole % based on the total amount of cobalt metal and said additive component in the catalyst composition, with an additive component concentration of from about 5% to about 25% being generally preferred for many applications.

In the practice of the invention, the cobalt component and the additive component can be combined in various ways, preferably by a method of combination that brings the cobalt component, i.e., thorium-promoted cobalt, and the additive component into intimate contact in the catalyst composition. A generally preferred method of incorporation is to impregnate the cobalt, preferably thorium-promoted cobalt, with a solution of a soluble molybdenum or tungsten compound. For example, ammonium heptamolybdate is a commercially available compound that is very soluble and suitable for purposes of the invention. Thorium-promoted cobalt oxide is a preferred source of cobalt. Coprecipitation of molybdenum or tungsten with the cobalt is also possible, but the resulting catalyst does not appear to have the extended lifetime capability achieved with respect to the preferred embodiments of the catalyst composition. A physical mixing of the cobalt with the additive component may also be possible, but is less likely to be effective for the desired purpose and is generally less preferred.

Synthesis gas conversion operations can be carried out in the practice of the invention with the Fischer-Tropsch catalyst composition as herein disclosed and claimed at a reaction temperature within the range of from about 150° C. to about 400° C., preferably from about 240° C. to about 320° C. The conversion operations can be carried out at any convenient pressure level, as from about 0 to about 1,000 psig, typically at from about 0 to about 350 psig.

While other promoter materials such as potassium and sodium are known in the art, thorium is employed as a promoter for the cobalt metal component in the practice of the invention. The most effective level of promotion appears to be obtained when about 15% $ThO_2$ is employed based on the weight of cobalt metal employed. The concentration of thorium can vary, however, from about 0.1 to about 15%, and some of the $ThO_2$ can be replaced with less expensive MgO provided that at least about 5% $ThO_2$ is retained for the desired promoter activity in preferred embodiments of the invention.

Prior to use of the Fischer-Tropsch catalyst composition in the syngas conversion process of the invention, the cobalt catalyst is reduced or activated by techniques employing hydrogen alone or together with other treating materials as is known in the art. For example, the catalyst may be activated by first combining with a low $H_2/CO$ ratio gas, or with CO alone, at a temperature in the range of about 250°–320° C. and a pressure of from 0 psig to the synthesis gas pressure. The catalyst is then further treated with hydrogen under similar temperature and pressure conditions. Further information regarding the preparation and activation of Fischer-Tropsch catalysts is provided in the published art, as in CATAL, REV.-SCI. ENG. 21(2), 225-274 (1980), "The Fischer-Tropsch Synthesis in the Liquid Phase", by Herbert Kolbel and Miles Ralek, particularly pp. 242–247 thereof.

In preferred embodiments of the invention, the Fischer-Tropsch catalyst composition desirably includes a support additive for said thorium-promoted cobalt and additive component admixture. In particularly preferred embodiments, said support component comprises a molecular sieve co-catalyst/support component rather than an inert support component such as α-alumina. The presence of such a co-catalyst material facilitates the desired conversion of syngas to liquid motor fuels. An especially desirable co-catalyst/support component for purposes of the invention comprises steam-stabilized, hydrophobic zeolite Y catalyst, sometimes referred to in the art as ultrahydrophobic type Y zeolites, or simply as UHP-Y zeolites. The cobalt, with or without thorium promotion, and the additive component may be positioned mainly in the large pores between the crystallites formed during the extrusion of the catalyst. It has also been found possible to place said cobalt and said additive component substantially within the crystallites of said UHP-Y zeolite as further discussed below. The Y zeolites used in this invention are prepared by extensive steaming of the low-sodium forms of zeolite Y substantially as described in Belgian Pat. No. 874,373, issued Feb. 22, 1979. Such zeolites are organophilic zeolitic aluminosilicate compositions having a $SiO_2/Al_2O_3$ molar ratio equal to or greater than 4.5, and an essential X-ray powder diffraction pattern of zeolite Y. Furthermore, the zeolites have a crystallographic unit cell dimension, $a_o$, of less than 24.45 Angstroms, a sorptive capacity for water vapor at 25° C. and a $p/p_o$ value of 0.10 of less than 10.0 weight percent. In preferred compositions, said unit cell dimension of the catalyst is from 24.20 to 24.35 Angstroms. In addition, the water adsorption capacity at 25° C. and a $p/p_o$ value of 0.10 is desirably less than 6.0 or even 4.0 weight percent. More particularly, the $SiO_2/Al_2O_3$ molar ratio for certain embodiments is from 4.5 to 20.0. In a desirable embodiment in which the UHP-Y zeolite is acid extracted as discussed below, the $SiO_2/Al_2O_3$ molar ratio may be extended up to about 100 or more, as the alumina content of the zeolite is generally reduced to less than about 3 weight % or even to about 1 weight % or less in practical commercial applications.

For the determination of the sorptive capacity of the hydrophobic zeolite Y compositions for any particular adsorbate, e.g. water, the test zeolite sample is activated by preheating at 425° C. for 16 hours at a pressure of 5 micrometers of mercury in a conventional McBain apparatus. The temperature of the sample is thereafter adjusted to the desired value and contacted with the vapor of the test adsorbate at the desired pressure.

The hydrophobic zeolites suitable for purposes of the invention, as described above, have also been found especially suited for use as adsorbents in applications where it is desired to preferentially adsorb organic constituents from solutions or mixtures thereof with water. In the formation of synthesis gas by the distillation of coal for example, it is desirable, for environmental and economic reasons, to recover the relatively small portion of phenol present in the condensate fraction of principally water that is produced therein. For this purpose, the condensate can be contacted at ambient temperature with said hydrophobic zeolite that will selectively adsorb the phenol from said condensate. Such zeolites have also been found highly suitable for use as base materials for catalyst compositions having important commercial applications, e.g. in midbarrel hydrocracking catalyst compositions. The UHP-Y zeolites described in particular detail in the Belgian patent referred to above have been found active for the conversion of methanol to hydrocarbons ranging from methane to those boiling in the jet fuel and diesel oil boiling range up to about $C_{22}$ material.

The invention is hereinafter described with reference to specific comparative tests that are presented to illustrate the invention and the advantages thereof. These illustrative comparative tests should not be construed, however, as limiting the scope of the invention as set forth in the appended claims.

EXAMPLE I

This example is presented as a comparative reference and is based on the conversion of syngas using a thorium-promoted cobalt catalyst supported on a UHP-Y co-catalyst/support component without the admixture of an additive component with said cobalt as in the practice of the invention illustrated in Example II below. For purposes of this Example I, the cobalt metal component was prepared by precipitation upon the addition of a 10% excess of sodium carbonate solution to a stirred room temperature aqueous solution of 400 g. of cobalt nitrate, i.e. $Co(NO_3)_2.6H_2O$. The cobalt oxide precipitate was washed with hot water and dried at 110° C. overnight. It was then impregnated with a thorium nitrate solution to provide a 15 wt. % thorium concentration, based on the weight of cobalt, on the precipitate, which was then dried at 110° C.

This thorium-promoted cobalt metal component was formed as ⅛" silica bonded extrudate containing 15% $CoO/ThO_2$, 70% UHP-Y zeolite and 15% by wt. silica binder. The resulting extrudate was dried at 110° C. for two hours.

80 cc of this catalyst was loaded into an internal recirculation reactor, in which it was treated, for cobalt activation, with hydrogen, at 300 psig, from room temperature up to 350° C., where it was held for 24 hours before cooling to 270° C. for treatment with 1:1 syngas. THe syngas was fed to the reactor at a rate of 400 cc/min or 300 GHSV, i.e. gas hourly space velocity, or volume of gas (at 0° C., 1 atm)/volume catalyst/hour. The conversion reaction was carried out at a pressure of about 300 psig and at a temperature of about 270° C. The results obtained in terms of the conversion of syngas, the primary product selectivity between hydrocarbons and $CO_2$, the hydrocarbon selectivity to the desirable $C_5^+$ range and other pertinent product characterizations are as set forth below, including Table I, under the various operating conditions recited in the Table.

TABLE I

| Run | 1 | 2 | 3 | 4 | 5 |
|---|---|---|---|---|---|
| Hours on Stream | 19.5 | 115.5 | 139.5 | 163.5 | 187.5 |
| Temperature, °C. | 272 | 269 | 269 | 270 | 269 |
| Feed, cc/min. | 400 | 400 | 400 | 400 | 400 |
| Conversion, wt. % | | | | | |
| on CO | 62.86 | 44.21 | 39.12 | 40.43 | 38.31 |
| on $H_2$ | 89.40 | 72.07 | 66.43 | 67.26 | 65.97 |
| on (CO + $H_2$) | 75.66 | 58.36 | 52.78 | 53.81 | 52.12 |
| Product Selectivity, wt. % | | | | | |
| $CH_4$ | 14.67 | 19.66 | 23.12 | 22.63 | 24.15 |
| $C_2$-$C_4$ | 13.23 | 12.86 | 15.47 | 13.70 | 14.59 |
| $C_5$–420° F. | 50.41 | 42.22 | 38.71 | 41.04 | 39.90 |
| 420–700° F. | 19.19 | 20.35 | 16.74 | 16.65 | 15.78 |
| 700° F.-end point | 2.51 | 4.91 | 5.95 | 5.98 | 5.58 |
| $C_5$-end Point | 72.10 | 67.48 | 61.41 | 63.67 | 61.26 |
| Iso/Normal Mole Ratio | | | | | |
| $C_4$ | 0.2857 | 0.1226 | 0.1778 | 0.1370 | 0.1327 |
| $C_5$ | 0.5572 | 0.2546 | 0.2698 | 0.2540 | 0.2473 |
| $C_6$ | 0.9660 | 0.4117 | 0.4181 | 0.4006 | 0.3892 |
| Paraffin/Olefin Ratio | | | | | |
| $C_3$ | 0.6912 | 1.4156 | 1.1943 | 1.2831 | 1.2776 |
| $C_4$ | 0.4206 | 0.7010 | 0.7044 | 0.6503 | 0.6289 |
| $C_5$ | 0.5004 | 0.7141 | 0.6954 | 0.6438 | 0.6146 |

Those skilled in the art will appreciate that the gasoline end point is about 420° F., while the diesel oil end point is about 200° F. It will also be appreciated that the 420°–700° F. hydrocarbon material comprises molecules with more carbon atoms than $C_{10}$ hydrocarbons up to about $C_{22}$ material. Hydrocarbon material in the $C_{22}$-$C_{28}$ range generally comprises heavy distillate material, with material above $C_{28}$ generally comprising wax.

The catalyst of this example showed an initial deactivation and an increase in methane production. The selectivity to condensed products was high, but the condensed products obtained contained undesired solids therein. The total condensed product was distilled and fractionated into gasoline (initial boiling point −420° F.), jet fuel (300°–550° F.) and diesel oil (300°–700° F.) fractions. The gasoline fraction contained 36.4% olefins upon FIA, i.e., Florescence Indicator Absorption analysis. Under such analysis, the jet fraction contained 31.6% olefins and had a pour point of 0° F. It will be appreciated that the pour point is the lowest temperature at which the liquid will flow. The diesel fraction had a pour point of 50° F. With such a high pour point, the diesel oil fraction could not be pipelined at low temperature.

EXAMPLE II

In this comparative example illustrating the practice of the invention, the adsorbent composition was prepared as in Example I above, except that the thorium-promoted cobalt component was impregnated with a solution of ammonium heptamolybdate to provide a 15% by weight deposition of molybdenum on the $CoO/ThO_2$ component. The thus-impregnated Fischer-Tropsch metal component was dried and formulated into an extruded catalyst as in said Example I. The catalyst loading, pretreatment and testing for syngas conversion were also essentially as set forth in Example I. The results obtained are set forth in Table II below:

TABLE II

| Run | 1 | 2 | 3 | 4 | 5 | 6 | 7 | 8 | 9 | 10 |
|---|---|---|---|---|---|---|---|---|---|---|
| Hours on Stream | 17.0 | 74.0 | 122.0 | 146.0 | 185.0 | 215 | 258.5 | 307.5 | 354.8 | 426.0 |
| Temperature, °C. | 270 | 269 | 270 | 270 | 270 | 270 | 270 | 269 | 269 | 269 |
| Feed, cc/min. | 400 | 400 | 400 | 400 | 400 | 400 | 400 | 400 | 400 | 400 |
| Conversion, wt. % | | | | | | | | | | |
| on CO | 67.21 | 55.09 | 51.71 | 51.48 | 49.81 | 48.82 | 48.47 | 44.98 | 43.85 | 42.02 |
| on $H_2$ | 82.61 | 77.73 | 75.32 | 75.35 | 74.06 | 73.00 | 72.46 | 69.44 | 68.54 | 67.52 |
| on (CO + $H_2$) | 75.19 | 66.84 | 63.93 | 63.82 | 62.42 | 61.41 | 60.98 | 57.65 | 56.63 | 55.20 |
| Product Selectivity | | | | | | | | | | |
| $CH_4$ | 14.00 | 17.04 | 18.34 | 18.20 | 19.99 | 20.41 | 20.34 | 21.47 | 22.74 | 24.00 |
| $C_2$-$C_4$ | 16.08 | 18.20 | 18.89 | 18.51 | 19.21 | 19.61 | 19.13 | 21.41 | 21.88 | 22.57 |
| $C_5$–420° F. | 50.88 | 48.12 | 48.39 | 48.01 | 46.34 | 46.61 | 47.62 | 45.44 | 43.74 | 42.56 |
| 420° F.-700° F. | 16.31 | 14.33 | 12.41 | 13.20 | 12.45 | 11.45 | 11.01 | 9.89 | 9.93 | 9.30 |
| 700° F.-end point | 2.73 | 2.31 | 1.97 | 2.07 | 2.01 | 1.92 | 1.90 | 1.79 | 1.70 | 1.57 |
| $C_5$-end point | 69.92 | 64.76 | 62.77 | 63.29 | 60.80 | 59.98 | 60.53 | 57.12 | 55.38 | 53.43 |
| Iso/Normal Mole Ratio | | | | | | | | | | |
| $C_4$ | 0.2051 | 0.1383 | 0.1154 | 0.1083 | 0.0963 | 0.1000 | 0.0914 | 0.0448 | 0.0815 | 0.0771 |
| $C_5$ | 0.4293 | 0.2618 | 0.2199 | 0.2101 | 0.1680 | 0.1634 | 0.1573 | 0.1414 | 0.1522 | 0.1412 |
| $C_6$ | 0.8211 | 0.4066 | 0.3208 | 0.2929 | 0.2642 | 0.2527 | 0.2294 | 0.2181 | 0.2079 | 0.1174 |
| Paraffin/Olefin Ratio | | | | | | | | | | |
| $C_3$ | 1.1915 | 0.9740 | 0.9481 | 0.9506 | 0.9195 | 0.9303 | 0.9297 | 0.9590 | 0.9077 | 0.8321 |
| $C_4$ | 0.6064 | 0.4851 | 0.4752 | 0.4787 | 0.4719 | 0.4615 | 0.4685 | 0.4617 | 0.4648 | 0.4650 |
| $C_5$ | 0.7138 | 0.5197 | 0.4852 | 0.4779 | 0.4687 | 0.4648 | 0.4672 | 0.4665 | 0.4918 | 0.5468 |

It will be seen from the results of Example II as compared with those of Example I, the catalyst of the invention did not show the rapid initial deactivation and increase in methane selectivity seen in the use of the reference catalyst of Example I. The $C_4$ hydrocarbons will be seen to be much more olefinic than in Example I, and the paraffin/olefin ratio in the Example II runs tends to decline appreciably and then remain relatively constant over the course of a relatively long period of on stream performance, whereas the ratio tends to increase appreciably and then to level off in the reference runs of Example I. The condensed liquid samples of Example II were combined and distilled into gasoline, jet and diesel oil fractions as in Example I. The gasoline fraction contained 48.3% olefins and the jet fraction contained 43.6% olefins, both significantly higher amounts than were obtained in the reference runs of Example I. The pour point of the jet fraction is $-10°$ F., and that of the diesel oil is 20° F., again representing significant improvements as compared to the reference runs. It will thus be appreciated that the process and catalyst composition of the invention provide a convenient and effective means for achieving the objects stated above, namely the improving of syngas conversion operations by enhancing the olefinic content of the liquid hydrocarbon conversion products obtained. The significant advantages obtained by the practice of the invention with respect to the olefinic content of the liquid products is further enhanced when the Fischer-Tropsch catalyst composition contains a molecular sieve material therein, as in the comparative examples, since the molecular sieve can act upon olefins much easier than it can act upon paraffins for the production of more desirable liquid motor fuel materials.

Those skilled in the art will appreciate that various changes and modifications can be made in the details of the invention without departing from the scope of the invention as set forth in the appended claims. Thus, as noted above, the desired enhancement of the olefinic content of the liquid hydrocarbon products can be facilitated by the use of a modified UHP-Y co-catalyst/support component or by the use of other such desirable support components. For example, the UHP-Y zeolite referred to above can be employed in aluminum-extracted form. Furthermore, the cobalt and said additive component can be positioned substantially within the crystallites of the UHP-Y zeolite or of the aluminum-extracted form thereof, and not merely within the large pores between the crystallites formed during extrusion of the catalyst, thus enhancing catalyst stability. In general when a co-catalyst/support is employed, the cobalt metal component will be employed in an amount within the range of from about 1% to about 25% by weight based on the overall weight of the catalyst composition, with cobalt concentrations of from about 5% to about 15% being generally preferred for most applications. When a co-catalyst/support component is not employed, from about 1% to about 100% cobalt by weight is useful, based on the total weight of cobalt, inert metal and possibly other additives, with about 5% to about 50% cobalt being preferred.

For purposes of achieving the aluminum-extracted form of said UHP-Y zeolite, the zeolite is conveniently acid washed or extracted essentially by the process as described in the Eberly patent, U.S. Pat. No. 3,591,488, to remove a large portion of the alumina from its pores prior to treatment to incorporate the metal component therein. By employing a suitable cobalt-containing liquid, such as cobalt carbonyl or a solution of cobalt nitrate or other cobalt salt, the metal can be positioned substantially within the crystals, and absorbed therein to form a very stable co-catalyst/support composition highly advantageous for the purposes of the invention.

In an illustrative example, UHP-Y molecular sieve zeolite was refluxed in a 13% slurry of said sieve in 3.75M hydrochloric acid for three hours. The slurry was then cooled, and the supernatent was decanted therefrom. The remaining slurry was diluted in half, filtered and washed chloride free with 0.001 of nitric acid. The slurry was then washed with distilled water, dried at 110° C. for 16 hours and then at 250° C. for 16 hours and at 500° C. for an additional two hours and bottled at 400° C. The thus-treated material comprised acid-extracted, substantially alumina-free, or aluminum-extracted, UHP-Y zeolite.

In preparing the catalyst composition of the invention in embodiments including a co-catalyst/support component, the cobalt metal component, promoted and admixed with said additive component, can be physically mixed with the co-catalyst/support component, as in the examples above, or can be precipitated on or pore filled on said co-catalyst/support component. For purposes of positioning the cobalt within the crystals of UHP-Y zeolite or the aluminum-extracted form thereof, a suitable cobalt solution can be loaded onto the zeolite by impregnation followed by heating or treatment with base. Addition of the inert metal and/or the thorium can be accomplished either during cobalt impregnation or separately thereafter.

Another advantageous co-catalyst/support component for purposes of the invention is a crystalline, microporous SAPO silicoaluminophosphate, non-zeolitic molecular sieve catalyst. Such catalyst materials, known as SAPOs and available at Union Carbide Corporation, are described in U.S. Pat. No. 4,440,871, issued Apr. 3, 1984, incorporated in its entirety herein. Individual members of the SAPO class are designated as SAPO-5, SAPo-11, SAPO-17, SAPO-20, SAPO-31, SAPO-34 and the like as disclosed in said patent. SAPO-11 and SAPO-31 are generally preferred for purposes of the invention, although it will be appreciated that other SAPOs, or combinations thereof alone or with other molecular sieves, may also be employed. It is, for example, within the scope of the invention to employ a steam-stabilized, hydrophobic zeolite Y, i.e. UHP-Y, as an additional co-catalyst/support component in addition to said SAPO material. In particular embodiments, the cobalt and said additive component admixed therewith are positioned inside said zeolite Y component, as for example inside the crystallites of the aluminum-extracted form thereof, with the thus-loaded UHP-Y co-catalyst/support component being used together with said SAPO or other suitable co-catalyst/support component.

It will be appreciated that such specific embodiments are intended to achieve the desired increase in the olefinic content of the liquid products obtained upon syngas conversion employing catalyst compositions of desirable stability and catalytic activity favorable to the production of the desired liquid motor fuels. In such specific embodiments and more generally, the invention utilizes a modification of cobalt not previously appreciated, in the context of syngas conversion and of the need for increasing the olefinic content of the products obtained, as providing the desired advance in the production of motor fuels from such syngas. The invention thus enables the hydrocarbon products of the Fischer-Tropsch syngas conversion reaction to be more olefinic than they would otherwise be using the Fischer-Tropsch catalyst as employed, but without the addition of molybedenum or tungsten as an additive component.

The invention thus represents a desirable advance in the art, enhancing the production of liquid motor fuels from syngas in an advantageous manner in light of the continuing need to meet the motor fuel requirements of industrial societies throughout the world.

I claim:

1. A synthesis gas conversion catalyst composition adapted for the enhanced catalytic conversion of synthesis gas comprising carbon monoxide and hydrogen to $C_5+$ hydrocarbon mixtures advantageous for use as liquid motor fuels comprising:
   (a) a Fischer-Tropsch catalyst component comprising cobalt, with or without thorium promotion; and
   (b) an additive component taken from the group consisting of molybdenum, tungsten and combinations thereof, said additive component being present in an amount within the range of from about 1% to about 50 mole % based on the total amount of cobalt and said additive component is said composition,
   whereby the olefinic content of the hydrocarbon products obtained is increased by the presence of said additive component, thereby enhancing the suitability of the resulting liquid hydrocarbons for use as motor fuels.

2. The composition of claim 1 in which said additive component comprises molybdenum.

3. The composition of claim 1 in which said additive component comprises tungsten.

4. The composition of claim 1 in which the concentration of said additive component is from about 5% to about 25%.

5. The composition of claim 2 in which said additive component comprises a combination of molybdenum and tungsten.

6. The composition of claim 1 in which the concentration of said additive component is from about 5% to about 25%.

7. The composition of claim 1 and including a support component for said cobalt and said additive component.

8. The composition of claim 7 in which said support component comprises a molecular sieve co-catalyst/support component.

9. The composition of claim 8 in which said co-catalyst/support component comprises a steam-stabilized, hydrophobic zeolite Y catalyst.

10. The composition of claim 9 in which said additive component comprises molybdenum.

11. The composition of claim 9 in which said co-catalyst/support component comprises said zeolite Y in aluminum-extracted form, said cobalt and said additive component being positioned substantially within the crystallites of said aluminum-extracted zeolite.

12. The composition of claim 11 in which said additive component comprises molybdenum.

13. The composition of claim 11 in which said additive component comprises tungsten.

14. The composition of claim 8 in which said co-catalyst/support component comprises a crystalline, microporous silicoaluminophosphate, non-zeolite molecular sieve catalyst.

15. The composition of claim 14 in which said catalyst comprises SAPO-11.

16. The composition of claim 14 in which said catalyst comprises SAPO-31.

17. The composition of claim 14 in which said additive component comprises molybdenum.

18. The composition of claim 14 in which said additive component comprises tungsten.

19. The composition of claim 14 and including a steam-stabilized, hydrophobic zeolite Y additional co-catalyst/support component.

20. The composition of claim 19 in which said zeolite Y component is in aluminum-extracted form said cobalt and said additive component being positioned substantially within the crystallites of said aluminum-extracted zeolite.

21. The composition of claim 20 in which the alumina content of said aluminum-extracted zeolite is less than about 3 weight %.

22. The composition of claim 19 in which the concentration of said additive component is from about 5% to about 25%.

23. The composition of claim 21 in which said additive component comprises molybdenum.

24. The composition of claim 1 in which said cobalt is thorium-promoted cobalt.

25. The composition of claim 9 in which said cobalt is thorium-promoted cobalt.

26. The composition of claim 11 in which said cobalt is thorium-promoted cobalt.

27. The composition of claim 21 in which said cobalt is thorium-promoted cobalt.

* * * * *